United States Patent [19]

Schumann et al.

[11] Patent Number: 4,460,274
[45] Date of Patent: Jul. 17, 1984

[54] PROCESS FOR THE LUMINESCENSE-SPECTROSCOPIC EXAMINATION OF COATINGS AND COATING PROFILES

[75] Inventors: Hans-Joachim Schumann, Cologne; Manfred Faust, Bergisch Gladbach, both of Fed. Rep. of Germany

[73] Assignee: Agfa-Gevaert Aktiengesellschaft, Leverkusen, Fed. Rep. of Germany

[21] Appl. No.: 310,140

[22] Filed: Oct. 9, 1981

[30] Foreign Application Priority Data

Oct. 15, 1980 [DE] Fed. Rep. of Germany ....... 3038908

[51] Int. Cl.³ ............................................. G01N 21/64
[52] U.S. Cl. .................................... 356/318; 250/459.1
[58] Field of Search ............... 356/317, 318, 320, 322, 356/326; 250/302, 458.1, 459.1

[56] References Cited

U.S. PATENT DOCUMENTS

| | | | |
|---|---|---|---|
| 3,341,705 | 9/1967 | Alburger | 250/302 |
| 3,386,920 | 6/1968 | Alburger | 250/302 X |
| 3,975,098 | 8/1976 | West | 356/320 X |
| 4,037,960 | 7/1977 | Macemon | 356/318 |

FOREIGN PATENT DOCUMENTS 0140917  4/1980 German Democratic Rep. ................. 250/358.1

OTHER PUBLICATIONS

Smith, "Luminescence Spectroscopy a Versatile Analytical Tool", Research/Development, pp. 20-27, Jul. 1968.
Smart, "Measurement of Thin Liquid Films by a Fluorescence Technique", Wear, vol. 29, #1, pp. 41-47, Jul. 1974.

Primary Examiner—Vincent P. McGraw
Assistant Examiner—L. A. Dietert
Attorney, Agent, or Firm—Connolly & Hutz

[57] ABSTRACT

The invention relates to a process for luminescence-spectroscopic examination and determination of coatings and coating profiles of solid and liquid layers and layer assembles whereby the luminescent substances present in the layers are photoselectively probed and determined through emission product spectra in incident and/or transmitted light by a photon detector using an emission spectroscopic process and whereby the photoselectivity of the luminescence-spectroscopic process being based on the substance related choice of the difference in wavelength $\Delta \lambda$ between the emission wavelength $\lambda_e$ and the excitation wavelength $\lambda_a$.

7 Claims, 14 Drawing Figures

PROCESS FOR THE LUMINESCENSE-SPECTROSCOPIC EXAMINATION OF COATINGS AND COATING PROFILES

This invention relates to a process for the luminescence-spectroscopic examination and determination of coatings and coating profiles of solid and liquid layers and layer assemblages and for detecting coating errors in layers and layer assemblages.

These are several known, partly automatic apparatus and processes for examining coatings on webs of material, their transverse and longitudinal profile as well as any local flaws therein, such as streaks and spot faults.

When applied to multiple-layer coatings, radiometric processes, such as $\beta$- and $\gamma$-ray absorption or X-ray fluorescence, which enable a coating of an individual layer to be examined through absorption measurement, back-scatter measurement or through excitation of the X-ray fluorescence radiation, provide only a token insight into the surface density, concentration or overall coating averaged out over all the coatings of the layer assemblage. Another disadvantage lies in the fact that the high decay rates of the radioisotopes or high beam intensities of the X-ray tubes which are necessary to guarantee adequate resolution of the measured values can only be used with commensurate caution in laboratories and factories. In addition, in view of the size of the measuring field, the processes in question frequently fail to satisfy the need for good local resolution of the layer thickness measurement. Moreover, the practical application of the processes in question always has to be carefully considered on account of the danger of actinic exposure.

Another widely used process for examining layer thicknesses and profiles is photometric measurement in the IR-region. With a multichannel arrangement, however, it is again only possible to differentiate between the individual layer coatings in the multiple layer assemblage providing the individual coatings can be distinguished from one another through special absorption characteristics, which is not the case for example with conventional photographic products. A two-channel measurement in and adjacent the water band for examining silver halide emulsions is disclosed in German Auslegeschrift No. 1,245,176. In this case, an individual coating is examined independently of underlying, already dry emulsion layers by comparative analysis of absorption and scattering. An arrangement which measures the scattering of the layer is also unsuitable for examining individual layers in multiple-layer assemblages or can only provide a token insight into any silver-containing emulsion layers.

British Pat. No. 1,482,462 describes another process for measuring the layer thickness of individual layers in multiple-layer assemblages. Although this known process can also be non-destructively applied to photographic products through the use of known highly sensitive detectors and with below-threshold exposure, it can only be successfully applied when the layers in question each have their own colour and adequate absorption differing from those of the other layers.

It is also known that spectroscopic processes can be used for examining coatings and coating profiles of layers and layer assemblages. These processes use for absorption, transmission or reflection of the substances in these layers. In these known processes, the measured value is determined from a ratio or difference measurement of the sample containing the substance in question relative to a comparison sample free from the substance in question. In the case of thin layers and low absorption coefficients, this comparative measurement leads to systematic errors when the measured values of the sample and comparison sample are close to one another. It is also difficult to prepare comparison samples which differ from the sample solely in the substance to be determined. In addition, the absorption measurements lack selectivity where several substances absorbing in the same spectral region are present, so that any deviation cannot be attributed to the incorrect dosage of a certain substance.

The sensitivity of absorption and remission measurements is not very high. Commercial apparatus have an overall accuracy of $\log_{10}(\Phi_o, \lambda/\Phi_T, \lambda)$, the logarithm to base 10 of the ratio of the incident radiation $\Phi_o, \lambda$ to the transmitted radiation $\Phi_T, \lambda$, of rarely more than $10^{-3}$ units for an optical layer thickness of $10^{-2}$ m.

For molecules of average size, the molar decadic absorption coefficient rarely exceeds a value of $10^4$ mole$^{-1}$m$^2$. Accordingly, the minimal concentration $C_{min}$ under the LAMBERT-BEER Law amounts to $\geq 10^{-5}$ mole.m$^{-3}$. With the layer thicknesses of the order of $10^{-5}$ m which are normally encountered in photography, for example, the minimal concentration $C_{min}$ which has to be present to detect a substance amounts to $\geq 10^{-2}$ mole.m$^{-3}$.

Examining coatings and coating profiles of thin layers through the colour density in the layers has the disadvantage that, in the case of photographic materials, the measurements can only be carried out after a processing step (exposure, development, fixing and drying). However, effects which seriously falsify the measurement results can occur during the treatment in the processing step.

Processes for determining absorption or reflection without any measurement of a comparison sample, of the type described in the above-mentioned British Pat. No. 1,482,462 for coloured layer assemblages, cannot be compared in their substance selectivity with the process described herein and show minimal sensitivity. Processes of this type fail in any selective examination of the coatings of individual, different layers in layer assemblages comprising 2 or more layers, as present for example in photographic films and photographic papers.

An object of the present invention is to provide a process of the type mentioned at the beginning by which it is possible to carry out batch measurements or continuous measurements for examining coatings and coating profiles of layers and layer assemblages, the coatings in layer assemblages comprising various different layers being selectively examined in a single measurement, in addition to which the measurements enable the production of these layers or layer assemblages to be quality-controlled.

Starting out from a process of the type defined at the beginning, this object is achieved in accordance with the invention in that the luminescent substances present in or added to the layers and layer assemblages, such as spectral sensitisers, optical lighteners, dyes and auxiliaries, are photoselectively probed in incident light and/or transmitted light by a photon detector using an emission-spectroscopic process and are determined alongside one another by a single measurement.

It was surprising to the expert to find that, using emission spectroscopy with high emission quantum yields, quantities of substance of $10^{-12}$ mole.cm$^{-3}$ and, with a special arrangement, $C_{min}$ quantities of $10^{-16}$ mole.cm$^{-3}$ can still be safely detected by the process according to the invention. By virtue of its extreme sensitivity, the process according to the invention is suitable not only for measuring the profile of each layer in a large number of individual, successively cast layers, but it is also suitable for detecting even minute variations in any of the layers such as can arise for example through flaws.

One particularly effective embodiment of the process is distinguished by the fact that the substances required for the process, such as optical lighteners, spectral sensitisers and dyes, are added to the solutions used for forming the layers before they are applied in such low concentrations that the properties of the layers are not adversely affected.

By adding traces of substances, surprisingly it is possible to characterise easily the spectral emission of each individual layer in a multiple set of layers. By carrying out a measurement over the spectral region, it is possible to examine and measure the profiles, faults and other properties of the individual layers and to use the results for regulating, controlling or establishing a fault pass level.

To this end, it has been found to be particularly advantageous that the photoselectivity of the emission-spectroscopic process is based on the substance-related choice of the difference in wavelength $\Delta\lambda$, with $\Delta\lambda = \lambda_e - \lambda_a$, the emission wavelength $\lambda_e$ and the excitation wavelength $\lambda_a$ offset by the wavelength difference $\alpha\lambda$ being synchronously varied through the wavelength $\lambda$ and the emission being observed in incident light, causing that several spectrally different luminescent substances may be selectively and quantitatively determined alongside one another, preferably by a single measurement.

In one particularly preferred embodiment of the invention, the photoselectivity is adjusted by free choice of the wavelength difference $\Delta\lambda$.

In the context of the present invention, phase differences are always understood to be differences in wavelength.

The photoselectivity and the possibility of determining several substances emitting in different regions of the spectrum alongside one another, preferably by a single measurement, is due to the emission spectroscopic method.

The conventional emission spectroscopy (EMI=emission spectrum, EXCI=excitation spectrum) describes the method and, concerning the wavelength dependent sensitivity of the emission channel of the equipment in use, corrected photonflux density $\Phi_e$ in dependence upon the excitation wavelength $\lambda_a$ and the emission wavelength $\lambda_e$ the emission band.

$$\Phi_e = \Phi_e(\lambda_a, \lambda_e) \tag{1.}$$

The spectral photon emission flux $\phi_e, \lambda$ is equal to the partial differential quotient, i.e., $$\Phi_e, \lambda(\lambda_a, \lambda_e) = \left(\frac{\delta\Phi_e}{\delta\lambda_e}\right)_{\lambda_a} \tag{2.}$$

$\delta_e$ is a normalized form factor of the emission and is defined by the following equations $$\delta_e(\lambda_a, \lambda_e) = \frac{\Phi_e, \lambda}{\int_{\lambda_e} \Phi_e, \lambda, \sigma\lambda_e} \text{ and} \tag{3.}$$

$$\int_{\lambda_e} \delta_e(\lambda_a, \lambda_e) \sigma\lambda_e = 1 \tag{4.}$$

Accordingly, the equation for determining $\Phi_e, \lambda$ is:

$$\Phi_e, \lambda = C, \tau, \psi \cdot T_a(\lambda_a) \chi(a(\lambda_a)) p_e(\lambda_a) \delta_e(\lambda_a, \lambda_e) \tag{5}$$

in which C is a geometry factor, $\tau$ is the degree of transmission of all the optical devices in the measurement beam path and $\psi$ is the slit function, $T_a(\lambda_a)$ is the absolute intensity function of the excitation beam which is obtained by calibration with substances of which the emission quantum yield is known and the known spectral photonflux density of the excitation lamp. In addition, $\chi(a(\lambda_a))$ is an apparatus function which is dependent upon the decadic absorption coefficient $a(\lambda_a)$. The product $T_a(\lambda_a) \chi(a(\lambda_a))$ is thus proportional to the number of quanta absorbed. Finally, $p_e(\lambda_a)$ is the emission quantum yield as the ratio of the number of quanta emitted to the number of quanta absorbed.

Assume emitting substances characterised by the index B are present in a mixture of substances, the total decadic absorption coefficient a is characterised by the index t $$a_t = \sum_B a_B(\lambda_a) \tag{6.}$$

so that the emission form factor $\delta_{et}(\lambda_a, \lambda_e)$ may be calculated in accordance with the following equation:

$$\delta_{et}(\lambda_a, \lambda_e) = \frac{\sum_B a_B(\lambda_a) \phi_{eB}(\lambda_a) \delta_{eB}(\lambda_a, \lambda_e)}{a_t(\lambda_a) \phi_{et}(\lambda_a)} \tag{7.}$$

If it is possible in a mixture of substances to find an emission wavelength $\lambda'_e$ at which only this substance characterised by the index 2 emits, the following equation is obtained similarly to equation 7):

$$\delta_{et}(\lambda_a, \lambda_e') = \frac{a_2(\lambda_a) \phi_{e2}(\lambda_a) \delta_{e2}(\lambda_a, \lambda_e)}{a_t \cdot (\lambda_a) \phi_{et} \cdot (\lambda_a)} \tag{8.}$$

This conventional process is significantly simplified if, as in the process according to the invention, both the excitation wavelengths $\lambda_a$ and also the emission wavelengths $\lambda_e$ are simultaneously varied by a fixed phase relation $\Delta\lambda$ through the wavelength $\lambda$. A new spectrum is obtained from the excitation spectrum EXCI and the emission spectrum EMI, being a product spectrum of the excitation spectrum and the emission spectrum and being referred to hereinafter as EXEM (product of EXCI and EMI).

The emission photonflux density $\Phi\Delta e$ of this spectrum is the spectral photonflux density $\Phi_e, \lambda$ according to equation 5.) above integrated with respect to $\lambda_a$ in the limits $\lambda_1$ to $\lambda_2$ of the overlap range.

$$\Phi\Delta_e = \int_{\lambda_1}^{\lambda_2} \Phi_{e,\lambda}(\lambda_a, \lambda_a + \Delta\lambda) d\lambda_a \quad (9.)$$

The emission photonflux density $\Phi\Delta e$ is thus proportional to the quanta absorbed in this range and hence to the concentration of the emitting substance.

By fixing the calibration functions, it is also possible to determine the concentrations of substances in mixtures of substances or in layer assemblages.

If several substances emitting in different spectral regions are present in a mixture of substances or in a layer assemblage and if wavelengths $\lambda_{e1}, \lambda_{e2}, \lambda_{e3}, \ldots$ at which only a single substance emits among these substances may be photoselected by the suitable choice of the fixed wavelength relation $\Delta\lambda$. For example, in photographic layers for emulsion layers or layer packs which are sensitised in the blue, green and red regions of the spectrum, three spectrally different spectra are obtained by a single measurement in which the entire spectral region is covered using a defined phase relation $\Delta\lambda$.

One advantageous embodiment of the process is distinguished by the fact that unpolarised light is used for exciting the sample for emission and an angle $\alpha$ of 55° or 125° is selected for the direction of the emission to the excitation beam.

Using unpolarised excitation, emission is only independent of the angle of observation $\alpha$, based on excitation, when in the following equation $$\frac{\Phi_{e,\lambda}(\alpha)}{\Phi_{e,\lambda}(O)} = 1 + \tfrac{1}{4}R(3\cos_\alpha^2 - 1) \quad (10.)$$

the second summand is equal to zero. In this equation, R is the degree of anisotropy of emission, while $\Phi_e, \lambda(o)$ is the spectral photonflux density at total depolarisation. The ratio in equation 10.) becomes equal to "1" when the angle $$\alpha = \arccos \pm (\tfrac{1}{3})^{\frac{1}{2}} \quad (11.)$$

Accordingly, with an angle $\alpha$ of 55° or 125° to the unpolarised excitation, the determination of emission is independent of the intrinsic polarisation of the spectrometer.

Another advantageous embodiment of the process is characterised in that linearly polarised light is used for exciting the sample for emission and the emission beam is analysed for its polarisation in such a way that the plane of vibration of the electrical vector is either perpendicular or parallel to the optical plane defined by the direction of the excitation and emission beam.

At polarised excitation and determination of the photonflux density $\Phi_e, \lambda$ parallel and the photonflux density $\Phi_e, \lambda$ perpendicular to the direction of polarisation of the excitation beam, which is generally identical with the direction of the monochromator slot, the following relation applies to the overall emission:

$$\Phi_e, \lambda = \Phi_e, \lambda \text{perpendicular} + 2\Phi_e, \lambda \text{parallel}$$

The perpendicular and parallel photonflux densities should be corrected in regard to the degree of intrinsic depolarisation of the spectrometer.

In one particular embodiment, excitation of the sample for emission may be carried out with continuous or pulsed light sources and the photonflux density of the luminescence of the sample may be measured both by a photodetector or by a photomultiplier, a photodiode, a diode array or a vidicon.

The process may also be carried out using an optical set that, the sample is scanned by two gratings rotating about a fixed axis. The gratings should be offset from one another by the wavelength difference $\Delta\lambda$.

In addition matrix effects, such as variations in layer thickness and concentration, or from layers other than the layer in question may be eliminated by using the excitation light reflected from the sample as reference and hence correcting the emission of the sample.

To examining profiles continuously, for example the longitudinal profile or the transverse profile of a coated web, the process may be modified to the extent that the undulation of the coating is directly and continuously determined by selective probing with a fixed phase difference and with fixed excitation and emission wavelengths.

In this way, the process is simplified in this particular case. The excitation and emission wavelengths are selected best at maximum intensity of the substances in the individual layers.

From this way, any relative undulation or, after calibration, absolute undulation in the coating can be measured more quickly than would be the case if the entire spectral range had to be covered.

Surprisingly, the process according to the invention is also suitable for detecting coating faults in the individual layers, even where they are covered by other layers, providing the layers are scanned by lasers, dye lasers or by a very narrow band and the shape and size of the measuring spot beamed or radiated onto the layer is adapted to the faults to be detected.

The process according to the invention may thus be used for the on-line examination, recording and regulation of the individual coatings in the layer assemblage and for the specific on-line examination of spot, longitudinal and transverse flaws in the individual layers of the assemblage during the coating process.

Variations in layer thickness may be detected as they occur and eliminated by adjustment of the coating machine. The same applied to faults which may be noticed and corrected immediately after their appearance, in order to avoid considerable losses. The extreme sensitivity of the process provides for precision adjustment of the coating machine and for a considerable improvement in quality.

If the exciting light is selected in such a way that actinic exposure of a photographic material is avoided, the process according to the invention may also be used with considerable advantage for photographic materials, particularly because these materials are simultaneously coated with a number of layers in a single operation. One streak in one of the layers is sufficient to make the photographic material worthless. For the first time the process described makes it possible immediately and selectively to detect these and other errors or variations in layer thickness and to ensure their elimination.

The invention is described in more detail in the following with reference to the accompanying drawings and the examples extracted from experimental work. In the accompanying drawings.

Figure 1:
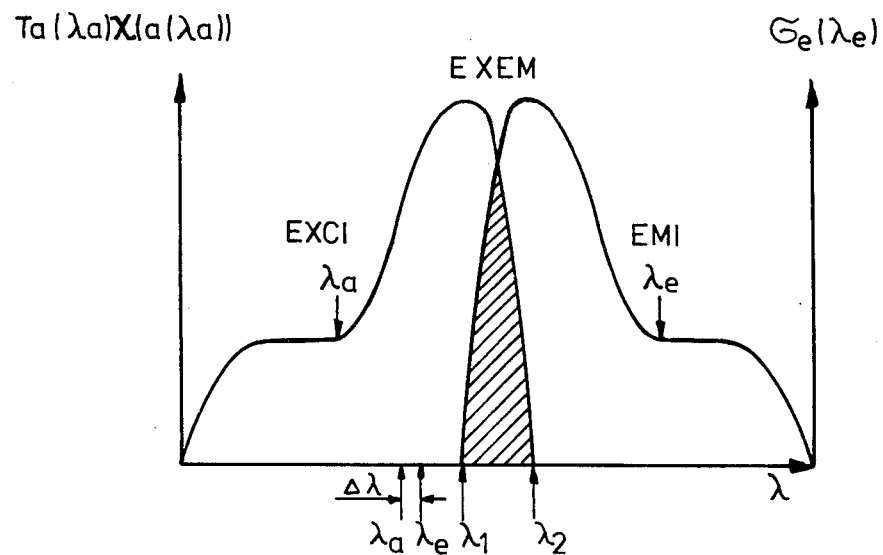
FIG. 1 is a perspective comparison between conventional emission spectroscopy and emission product spectroscopy with reference to the example of a sensitiser.

The excitation spectrum EXCI and emission spectrum EMI obtained by a conventional process are shown on the left and right, respectively, of FIG. 1. The process is considerably simplified if both the excitation wavelengths $\lambda_a$ on the left and also the emission wavelength $\lambda_e$ on the right are simultaneously varied with a fixed wavelength relation $\Delta\lambda$ through the wavelength $\lambda$. For example the result is a spectrum which corresponds to the overlap region (hatched) between the absorption or excitation spectrum, characterised by Ta $(\lambda_a)\chi$ $(a(\lambda_a))$, and the emission spectrum, characterised by $\delta_e(\lambda_e)$. The spectra are typical of numerous sensitisers and defined as emission product spectra EXEM.

Figure 2:
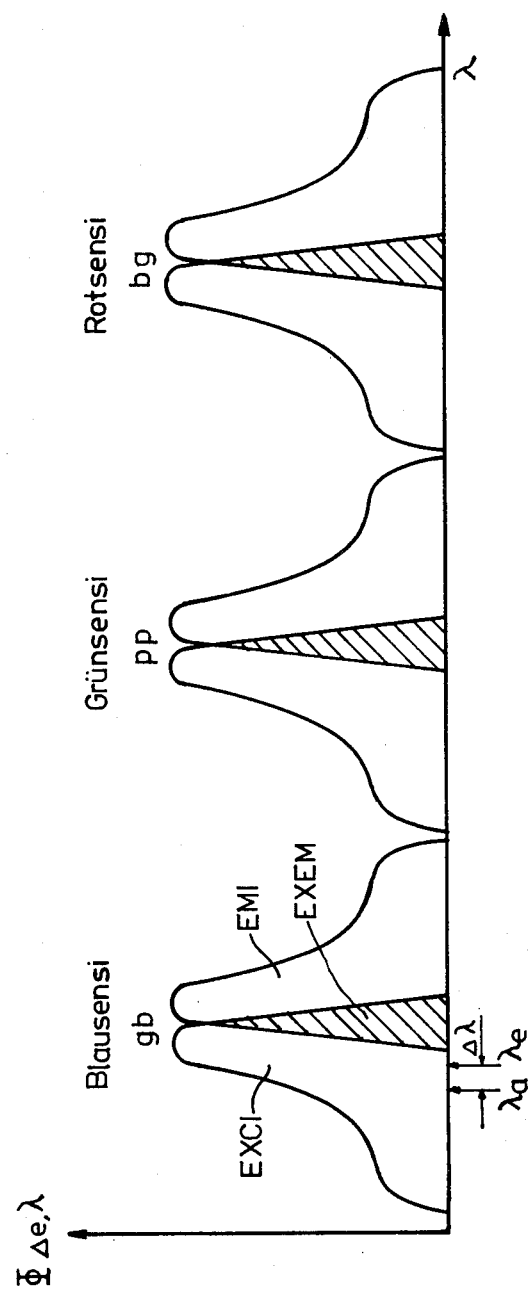
FIG. 2 shows an emission product spectroscopy on a blue-, green- and red-sensitised photographic material.

FIG. 2 shows three spectrally idealised spectra which are obtained by a single measurement covering the entire spectral region $\lambda$ with a defined wavelength relation $\Delta\lambda$ between $\lambda_a$ and $\lambda_e$. In this example, several mixed up substances which emit at different wavelengths are photoselected by the choice of the fixed wavelength relation. FIG. 2 is typical of photographic layers or layer packs which are sensitised in the blue, green and red spectral region and have their excitation and emission maximum in the yellow (gb), magenta (pp) and cyan (bg) region of the spectrum.

Figure 3:
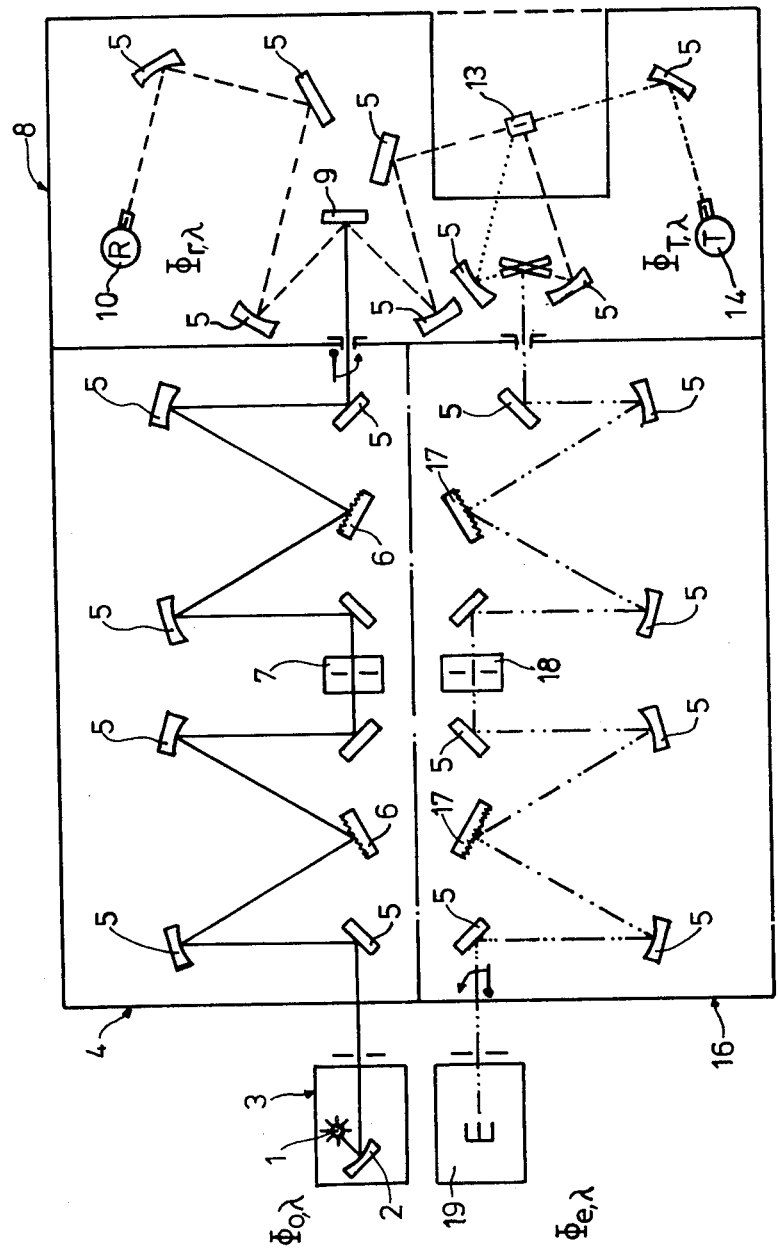
FIG. 3 shows an emission spectrometer used by way of example.

FIG. 3 shows an exemplary spectrometer for measuring emission manufactured by the Spex company in the USA. The apparatus consists essentially of a light source 1 in a housing 3, two double monochromators 4, 16, an excitation beam measuring system 10 in the housing 8, a sample housing 12, a transmission measuring system 14 and an emission detector 19.

The light of a high-pressure xenon lamp light source 1 is beamed through an elliptical mirror 2 into an excitation monochromator 4, where the light is dispersed through several elliptical and plane mirrors 5 in conjunction with two gratings 6, connected with an adjustable slot 7. The gratings 6 are provided with 1200 lines/mm and are blazed at 400 nm. From the monochromator 4, the light beam passes into a housing 8 and is subdivided into two beams by a beam splitter 9. One of these two beams is directed through mirrors 5 to a light quantum counter 10 for determining the photonflux density of the excitation beam. The light quantum counter 10 may be a rhodamine B photomultiplier unit (R) or a calibrated diode.

The second light beam is directed from the beam splitter 9 through deflecting mirrors 5 into a measuring chamber 12 where it is used for measuring the sample in incident light and/or to a right-angled arrangement in a thermostatically controlled film sample holder 13. The light passing through the sample may be measured in a transmission detector 14, for example by means of a rhodamine photomultiplier unit (T).

It is particularly advantageous to use this unit as a second reference channel. Thus the excitation light reflected by the sample falls onto the mirror 5 turned through a certain angle and then hits the rhodamine B photomultiplier unit (T). In this way, it is possible to eliminate matrix effects from layers other than the layer questioned.

The light emitted from the sample is directed to mirrors 5 into the emission monochromator 16 and to further mirrors 5 to a first grating 17, an adjustable slot 18, a second grating 17, and the emission detector 19. A photomultiplier is used as the emission detector 19.

The light pulses of the emission monochromator 16 are evaluated by a photon counting process.

The two monochromators 4, 16 are driven and synchronised by stepping motors so that the phase difference may be freely selected (not shown).

The stepping motor is controlled and the emission, reference and transmission signals are picked up after digitalisation by a 16-bit minicomputer (not shown).

The invention and its application are further illustrated in the following Examples based on experimental work.

EXAMPLE 1

Two layers were simultaneously applied by a coating machine (a cascade coater) to a 1370 mm wide polyethylene paper support.

The composition of the coating solution for the two layers was as follows:

Layer 1: green sensitiser GS dissolved in methanol so that a concentration of $10^{-2}$ mole.m$^{-3}$ was obtained with 4 ml/l of a 10% gelatin solution;

Layer 2: red sensitiser RS dissolved in methanol so that a concentration of $10^{-2}$ mole.m$^{-3}$ was obtained with 6 ml/l of a 10% gelatin solution.

The solutions were applied in a wet layer thickness of $40 \cdot 10^{-6}$ m per layer so that a dry layer thickness of $8 \cdot 10^{-6}$ m was obtained. A piece of web was cut across its width into 35 mm wide strips (wedges) and spectroscopically examined.

The spectroscopic measurements were carried out in the apparatus described above (FIG. 3), the unpolarised excitation beam forming an angle $\alpha$ of 55° with the emission beam.

The area illuminated on the sample measured $5 \times 10$ mm. The photonflux density $\Phi\Delta e,r$ was automatically corrected in regard to the fluctuation in intensity of the lamp by forming the quotient from the emission and reference photonflux density. The excitation slot was 5 nm wide and the emission slot was 2 nm wide. The difference in wavelength between excitation and emission amounted to $\Delta\lambda = 8$ nm.

Figure 4:
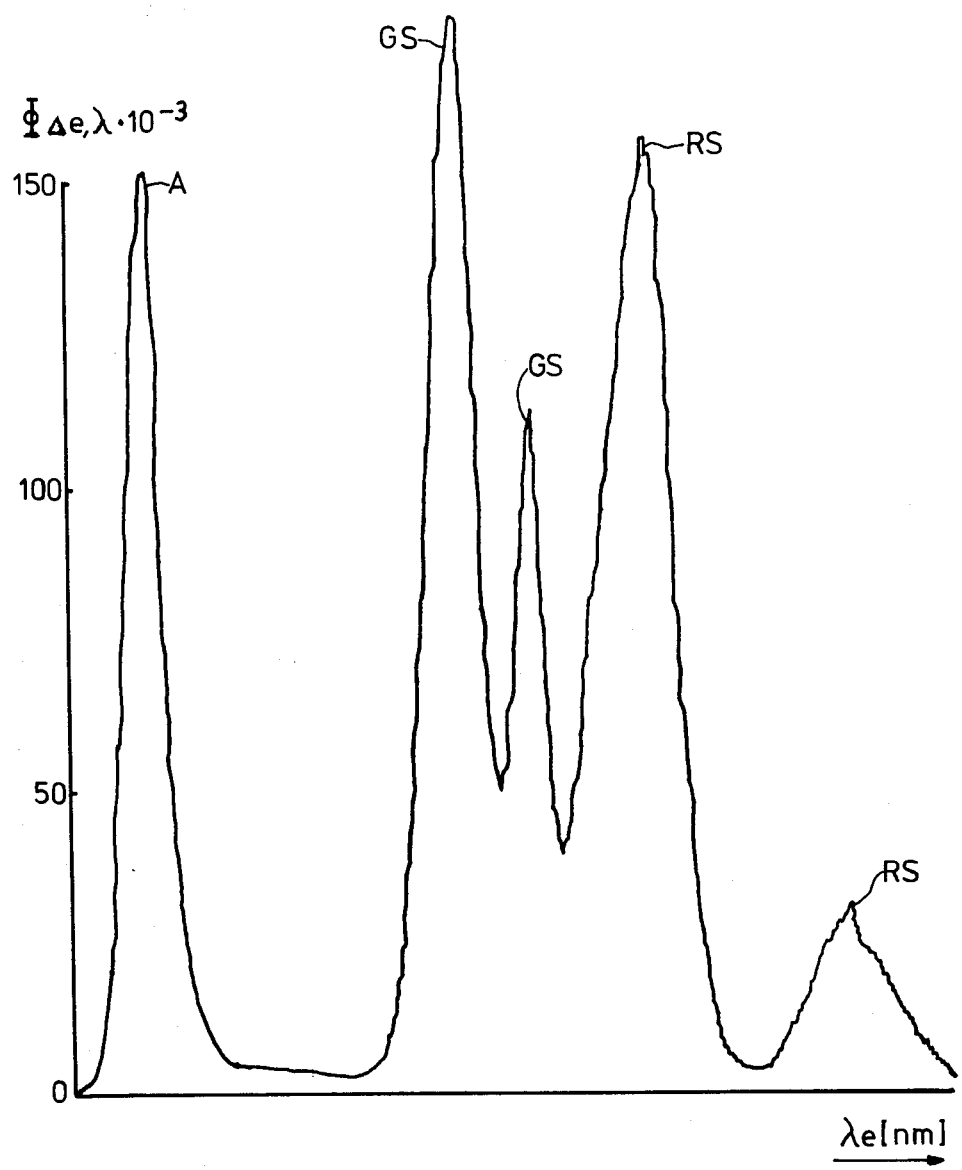
FIG. 4 shows the spectrum of a polyethylene support coated with two colour emulsions (Example 1)

A spectrum of a sample is shown in FIG. 4. The short-wave band is the emission of the optical lightener A in the paper felt of the support.

The two middle bands are the emissions of the green sensitiser GS whilst the long-wave bands are the emissions of the red sensitiser RS.

Figure 5:
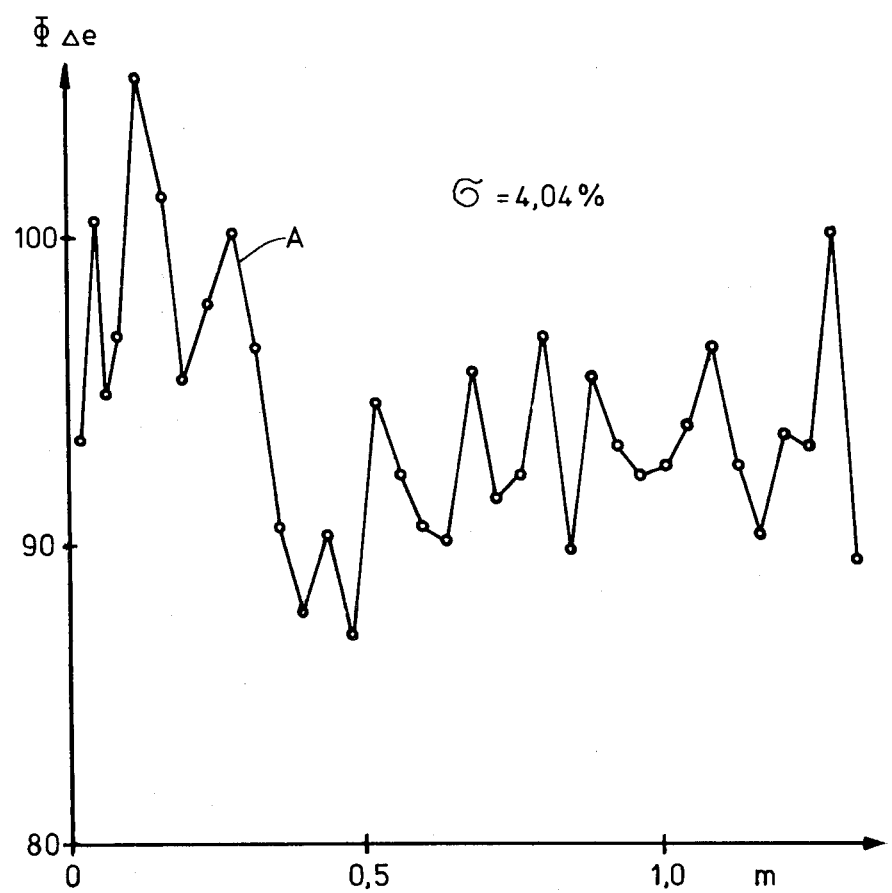
FIG. 5 shows the undulation of the polyethylene support as measured by the emission of the optical lightener (Example 1)
Figure 6:
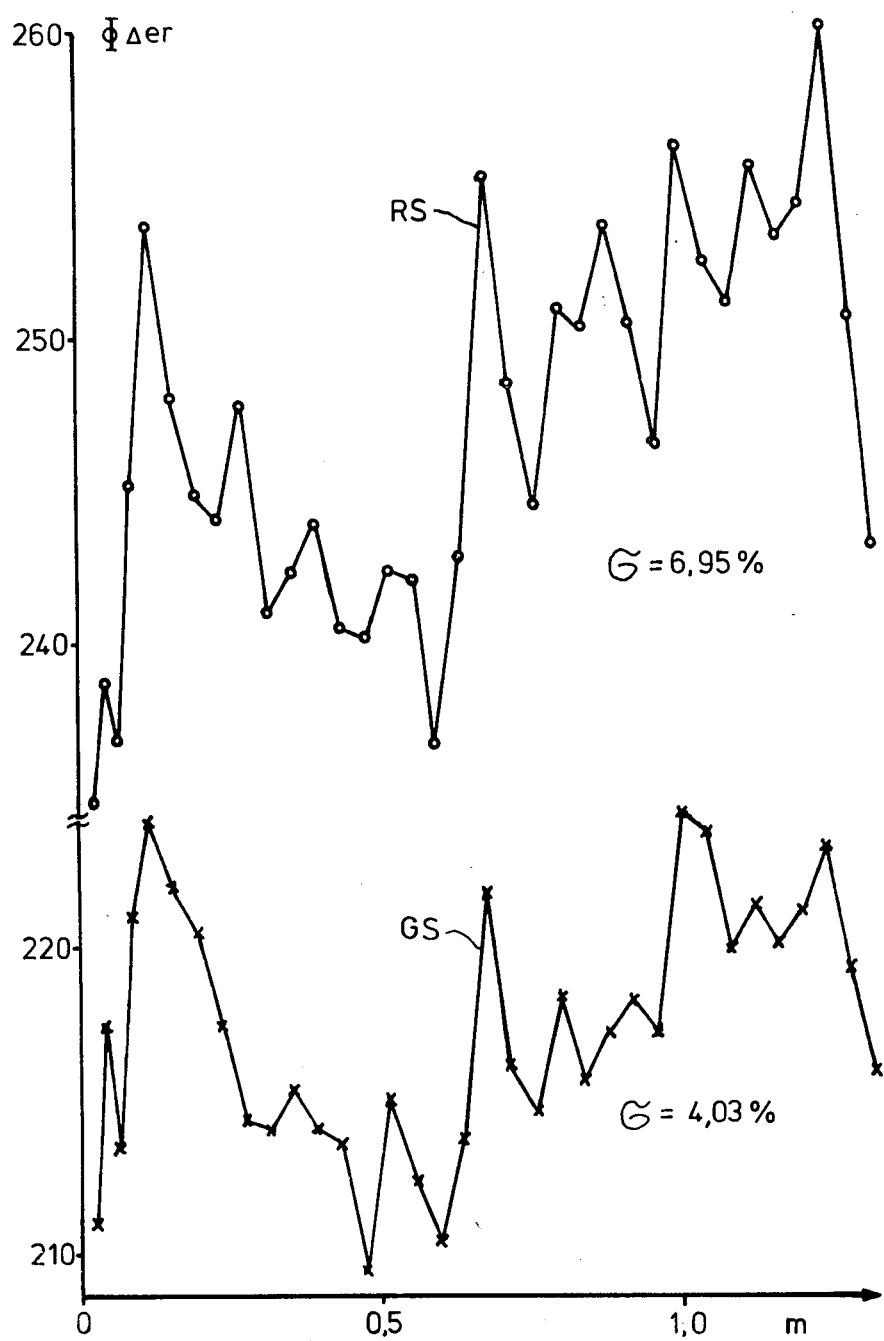
FIG. 6 shows the undulation of the colour layers as measured by the emissions of the sensitisers (Example 1)

The results of the measurements over the width of the web are shown in FIGS. 5 and 6. The coordinates of the emissions were evaluated in each case. The undulation A, the standard deviation of the optical lightener which corresponds to the variation in layer thickness of the paper support, is shown in FIG. 5 and amounts to $\delta = 4\%$. FIG. 6 shows the curves of the variations in thickness of the green sensitiser GS which corresponds to the layer thickness of the first layer and amounts to $\delta = 4\%$ and those of the red sensitiser RS which corresponds to the layer thickness of the second layer and amounts to $\delta = 7\%$.

Instead of using the sensitisers, it is possible to use other suitable luminescent substances in such low concentrations that the layer properties are not affected or, alternatively, the quality of the coatings can be tested under production conditions.

EXAMPLE 2

14 samples 89 mm wide were taken transversely of the coating direction from a 1370 mm wide, multiple-layer colour paper web on a polyethylene support and spectroscopically examined in the same way as in Example 1.

Figure 7:
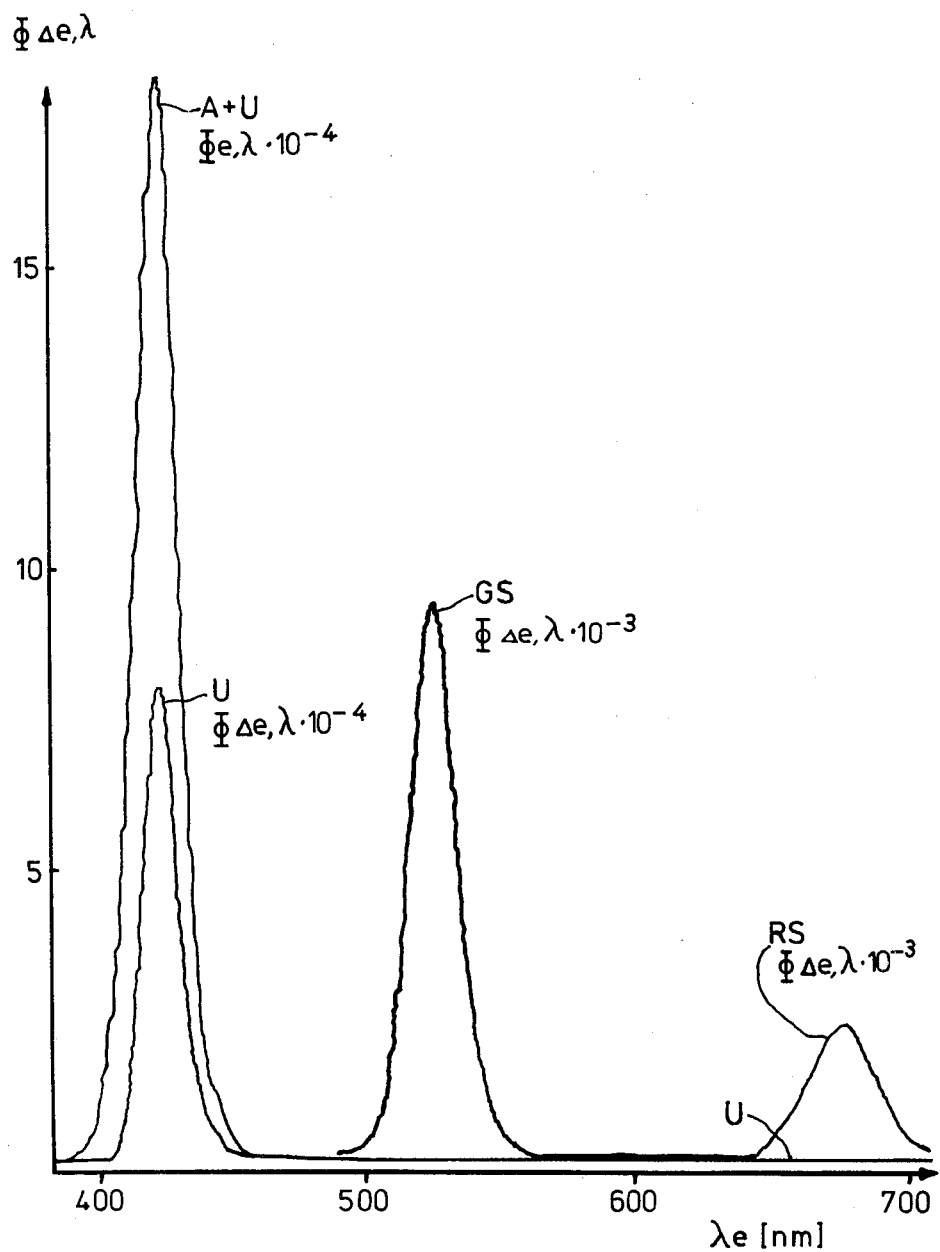
FIG. 7 shows the spectrum of the support of the lightener and the layers of a colour paper (Example 2)

A spectrum is shown in FIG. 7. The two short-wave bands at $\lambda_e \approx 420$ nm are the emissions of the optical lightener A in the layers and the support U, and of the support U alone.

The difference in the integral photonflux density between the two bands is proportional to the amount of optical lightener A in the individual layers of the layer assemblage.

The middle band at $\lambda \approx 520$ nm is the emission of the green sensitiser GS and the long-wave band at $\chi 680$ nm is the emission of the red sensitiser RS. The measurements for GS and RS were carried out with a higher sensitivity by a factor of 10.

Figure 8:
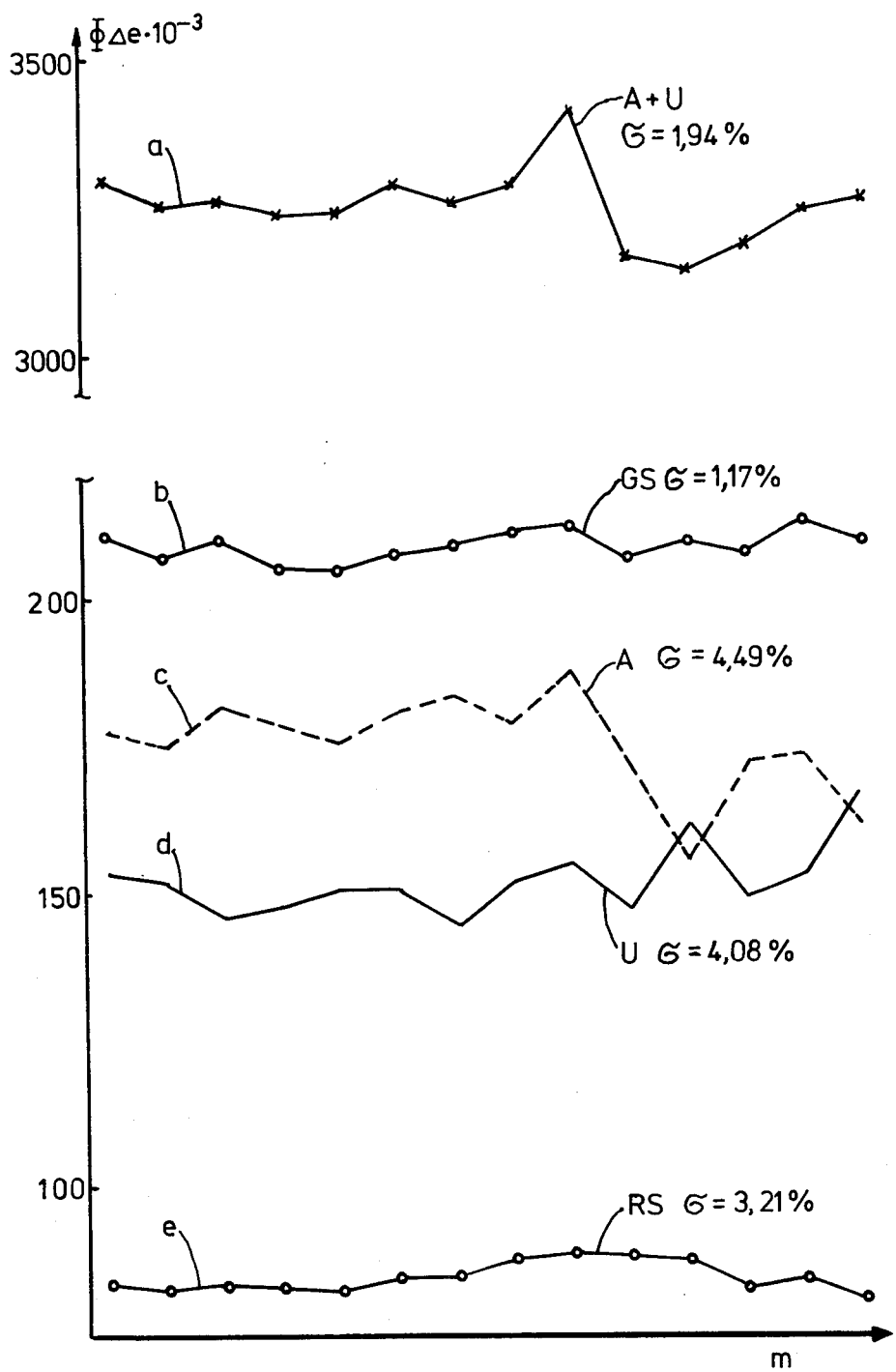
FIG. 8 shows the undulation of the support and the overall structure of the colour paper (Example 2)

In view of the clear separation between the bands, the integral photonflux densities of the emissions of the individual bands were determined and are shown over the width of the web in FIG. 8.

The curve in FIG. 8a reflects the undulation of the overall structure and of the support over the width of the web. The standard deviation $\delta$ amounts to 1.94%.

The curve in FIG. 8c shows the undulation of the layer assemblage A alone. The curve was obtained from the difference measurements of the overall assemblage (A+U) and the support U (FIG. 8d). The standard deviation $\delta$ amounts to 4.94%.

The curve in FIG. 8d reflects the undulation of the support with a standard deviation $\delta$ of 4.08%.

The curve in FIG. 8b shows the transverse profile of the magenta layer represented by the emission of the green sensitiser GS with a standard deviation $\delta$ of 1.17% whilst the curve in FIG. 8e shows the transverse profile of the cyan layer represented by the emission of the red sensitiser RS with a standard deviation $\delta$ of 3.21%.

EXAMPLE 3

Figure 9:
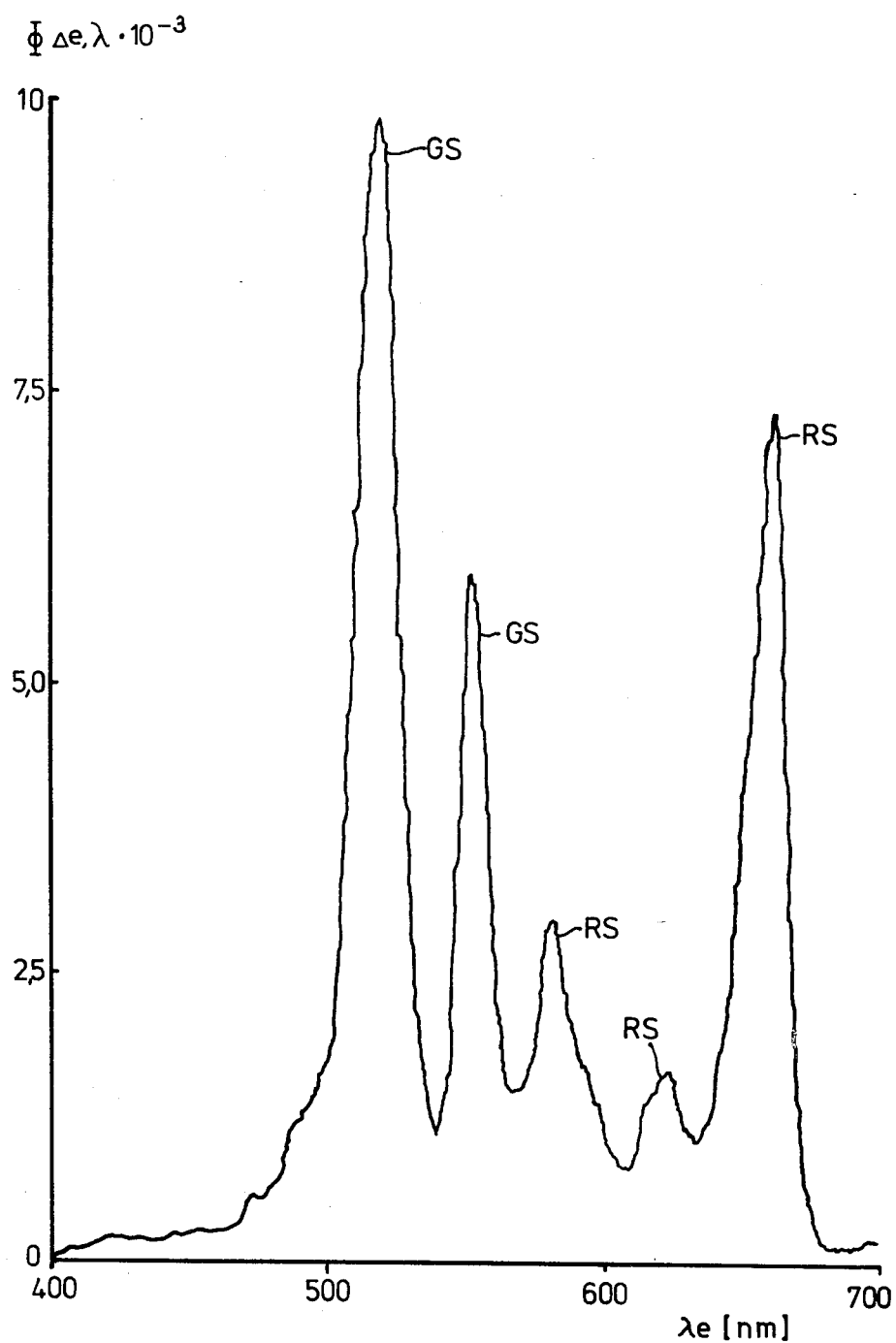
FIG. 9 shows the spectrum of a colour negative film (Example 3)

30 samples 35 mm wide were taken transversely from an 1100 mm wide multiple-layer colour negative web-form film and were spectroscopically examined in the same way as in Example 1. A spectrum is shown in FIG. 9. The bands at $\lambda = 520$ nm and $\lambda = 552$ nm are the emissions of the green sensitiser GS whilst the bands at $\lambda = 580$ nm, $\lambda = 620$ nm and $\lambda = 657$ nm are the emissions of the red sensitiser RS.

Figure 10:
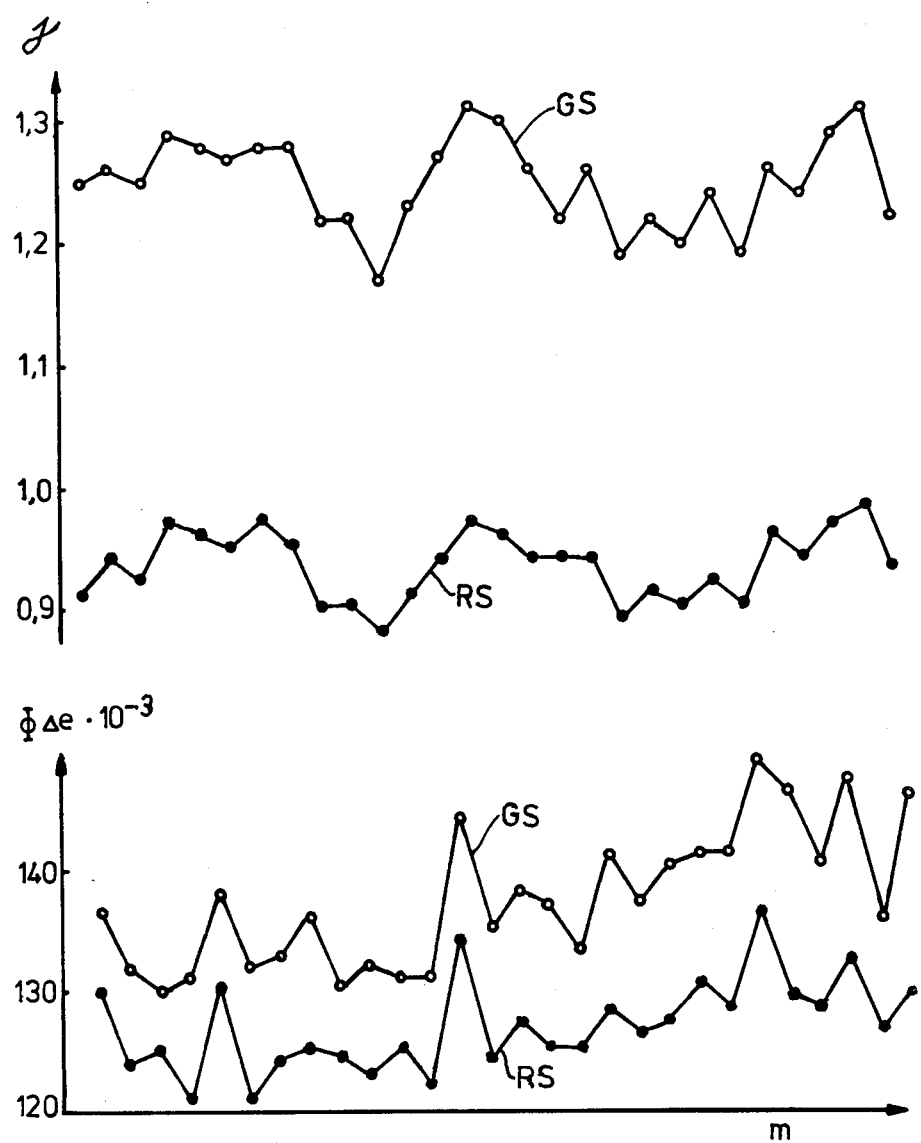
FIG. 10 shows the measurements of emission and gradation over the width of an unhardened web-form layer assemblage (Example 3)

FIG. 10 shows the emission measurements $\Phi\Delta e \cdot 10^{-3}$ of the samples over the width of the web.

The examinations were obtained for an unhardened layer assemblage for the magenta layer, the green sensitiser GS and the cyan layer, the red sensitiser RS. The gradation curve was plotted against the emission curve after developing at 20° C.

Figure 11:
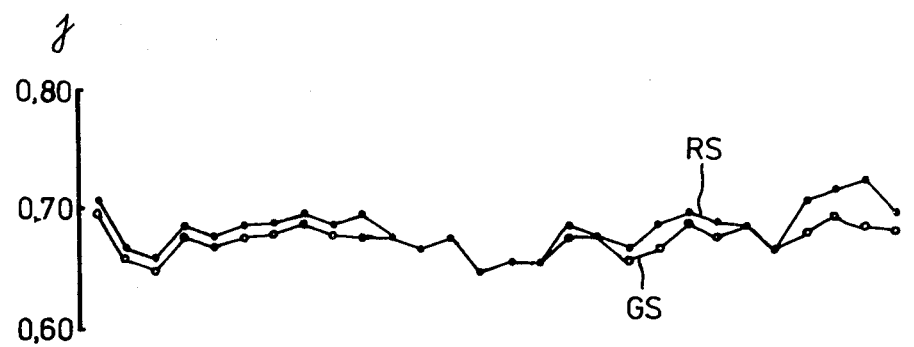
FIG. 11 shows the same measurements as FIG. 10 of a hardened layer assemblage (Example 3)
Figure 11:
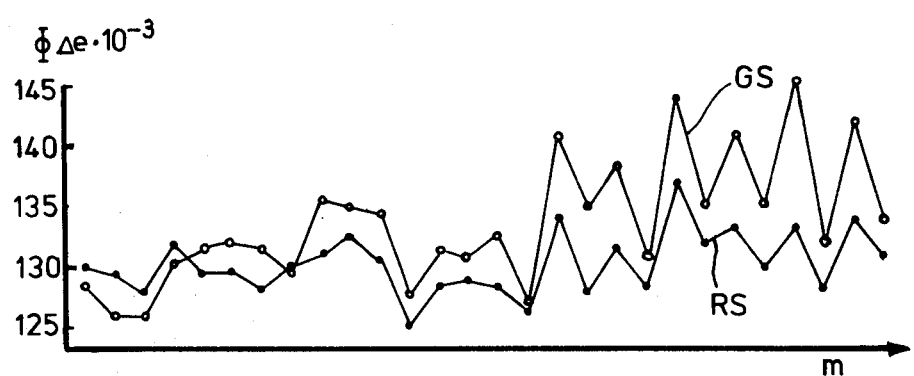

The measurements of an adjoining, but hardened strip of web over the width of the web are shown in FIG. 11. For comparison, the gradation curves with the gradation values $\gamma$ obtained after processing at 38° C. in a film developing machine were again plotted against the emission curves.

The undulations or standard deviations over the width of the web are as follows:

| Hardening | Layer | Standard deviation in % | |
|---|---|---|---|
| | | $\sigma$(Emission) | $\sigma$(Gradation) |
| unhardened | magenta | 4.2 | 3.3 |
| | cyan | 3.7 | 3.5 |
| hardened | magenta | 5.3 | 2.4 |
| | cyan | 3.2 | 2.4 |

Comparison of FIGS. 10 and 11 clearly shows that gradation depends to a very large extent upon the degree of hardening whereas emission shows virtually no dependence thereon. Accordingly, the undulation of the layer assemblage may be inspected both before and after hardening by means of emission measurements.

EXAMPLE 4

A 35 mm wide strip was taken from a 1130 mm wide polyethylene-supported colour paper web transversely of the direction of travel of the web. The composition of the web was as follows: support, cyan layer, protective layer, magenta layer, protective layer.

Figure 12:
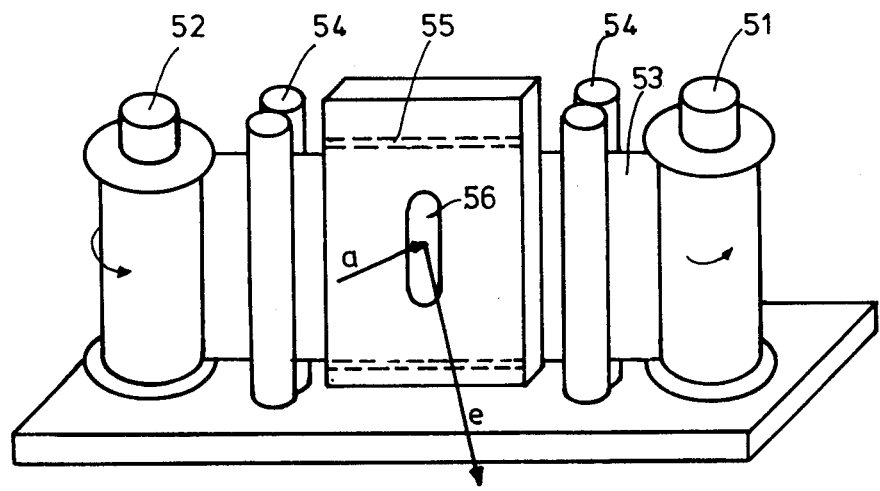
FIG. 12 shows an apparatus for continuously measuring emission over the width of the web.

For continuously examining the coating over the width of the web, the strip was introduced in the form of a roll into an apparatus of the type shown in FIG. 12.

FIG. 12 shows a delivery spool 51 and a take-up spool 52 for the strip 53 to be examined. Between the spools 51 and 52 there are guide rollers 54 and between these guide rollers 54 is the measuring plate 55 with means for pressing down the strip 53 flat. The measuring plate 55 is provided with a measuring window 56 onto which the excitation light beam a is directed and which produces the emission beam e on the measuring strip 53. This unit is introduced into the measuring chamber 12 of the apparatus shown in FIG. 3 and serves as a means for continuously examining strips cut from the web. The spools 51 and 52 are driven in the arrowed direction in the usual way by a synchronous motor (not shown).

The excitation beam a impinges on the strip 53 with an excitation light spot 2.5 mm wide and 10 mm long. The excitation and emission wavelengths are adjusted to maximum intensity (FIG. 7 and Example 2) and the strip 53 was examined under these conditions. The transverse profiles of the cyan and magenta layers and the total undulation of the coating of the optical lightener in the layer assemblage and in the support were then directly obtained.

The band widths for the cyan and magenta layers were 10 nm for excitation and 5 nm for emission. The phase difference $\Delta\lambda$ was 12 nm. The same slot widths and phase difference as in Example 2 were selected for the optical lightener.

Figure 13:
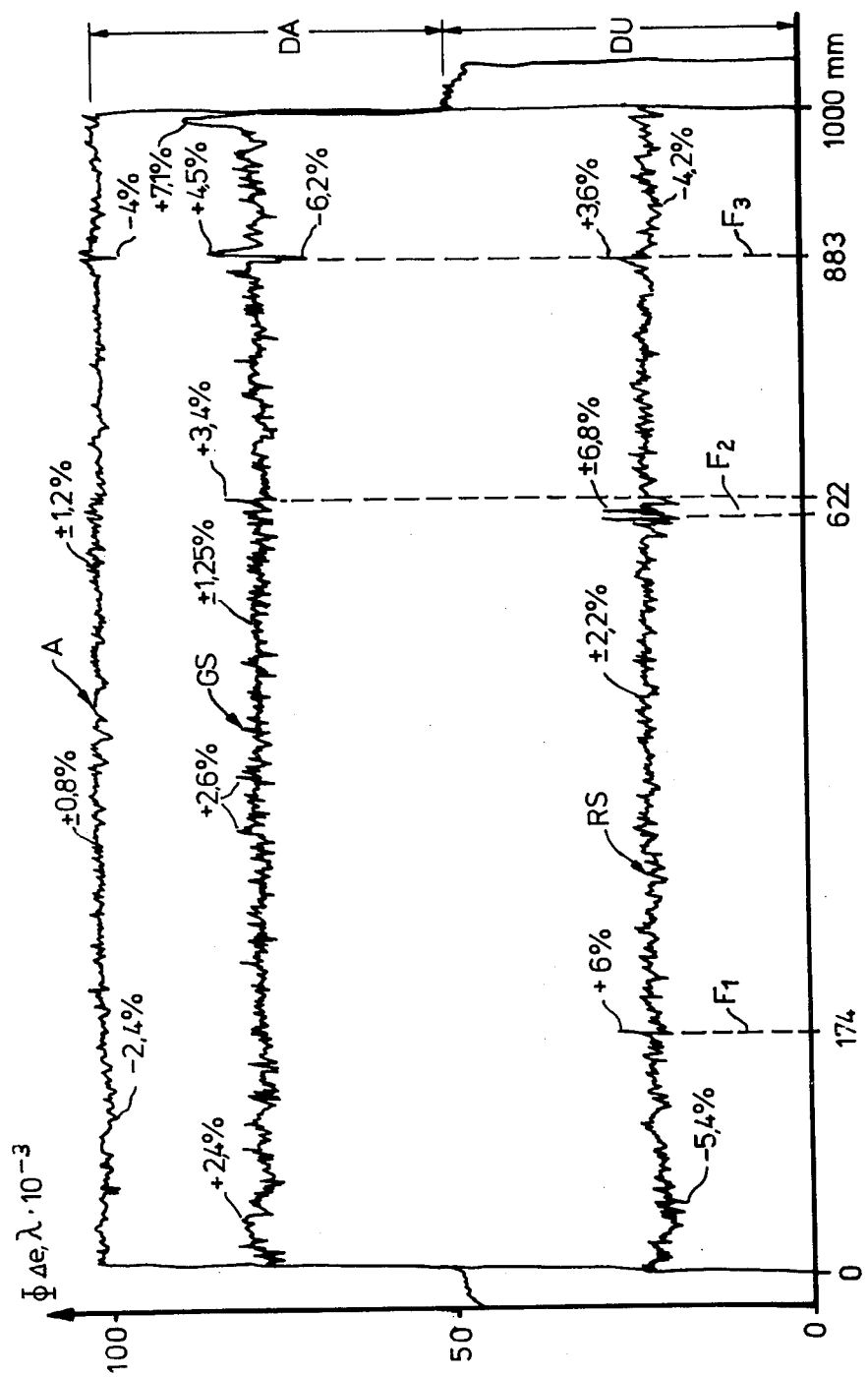
FIG. 13 shows continuous emission measurements over the width of the web for determining layer thickness and for detecting faults (Example 4)

Continuous measurements of the cyan layer (red sensitiser RS) over the width of the web is shown in FIG. 13 (lowermost curve RS). The distinct coating edges (coating width 1000 mm) are slightly superelevated and, on the right and left, show deviations of 4 to 5% from the mean value of which the average fluctuation amounts to about ±2%.

Coating flaws $f_{1-3}$ are noticeable at distances of 174, 622 and 883 mm from the lefthand edge of the web. The curve of the measurements of the green-sensitised layer GS is plotted over the lower curve RS.

Comparison of the measurements for the RS and GS layer shows that the coating flaw $F_1$ at 174 mm is only present in the RS-layer.

The coating flaws $F_2$ with the centre at 622 mm from the left-hand edge of the web occur most conspicuously in the RS layer, considerably less noticeably in the GS layer and not at all in the uppermost curve A for the optical lightener.

The flaw $F_3$ at 883 mm from the left-hand edge of the web is noticeable in all three curves RS, GS and A. This flaw $F_3$ is attributable to mechanical damage of the support before coating.

The flaws $F_{1-3}$ could be clearly confirmed after colour processing, ranging from 0.05 to 0.2 mm in width.

The percentage determined during the measurements and recorded in the curves for the flaws $F_{1-3}$ are only reference values in this case because, for accurately measuring a coating flaw, the probing width should amount to between one fifth and one third of the width of the coating flaw, although this requirement may readily be satisfied by using a laser.

Measurement of the magenta layer GS 5 (green sensitiser) shows that the edge of the coating from a thick ridge at the edges of the web. Except for the edge and the coating flaws F, the undulation is only 1 to 2% above the noise which lies at 1±0.2%.

Measurements of the optical lightener A is shown by the uppermost curve in FIG. 13. Measured values DU for the support only accumulate at the uncoated edge. Within the coating width from 0 to 1000 mm, curve A shows a superposition DA of the emissions of the lightener in the support and in the layer assemblage. This undulation is substantially commensurate with the total amount of silver present in the coatings of the assemblage.

Figure 14:
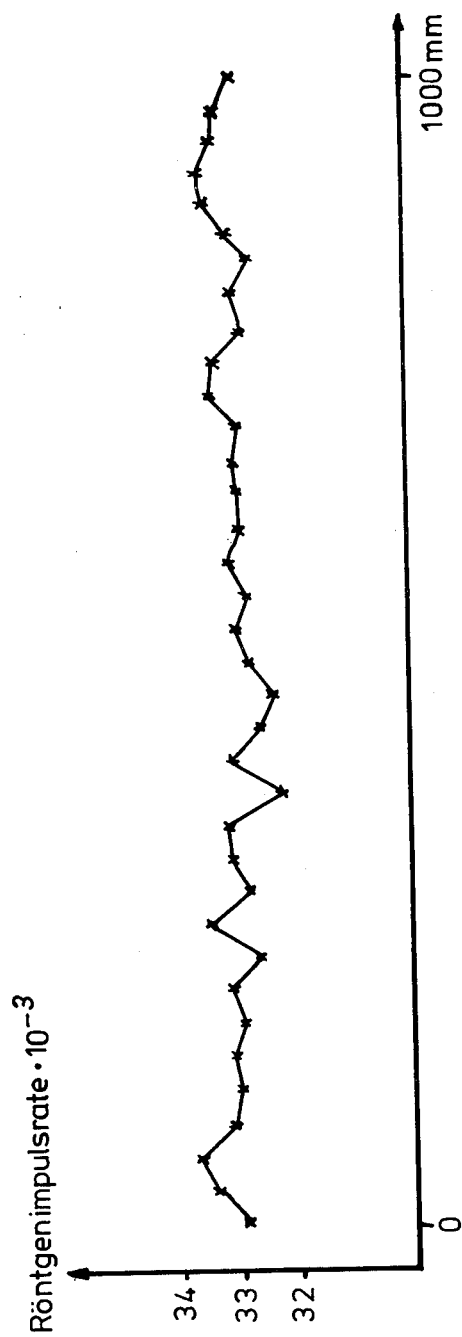
FIG. 14 shows the measurement of the silver in the coating for comparison with the emission measurement (Example 4).

FIG. 14 shows a curve in which the silver values as determined over the width of the web are recorded. To this end, the silver pulses from X-ray fluorescence were determined at 36 points over the width of the web using a window measuring 28×28 mm. Comparison of the curves in FIGS. 13 and 14 shows that the coating flaws F are no longer resolved. In the curve, a vertical difference of approximately 3.3 mm corresponds to a variation in the quantity of silver applied to ±1%.

We claim:

1. A process for the luminescence-spectroscopic examination of coatings and coating profiles of solid and liquid layers and layer assemblages, whereby the luminescent substances present in the layer and layer assemblages, such as spectral sensitisers, optical lighteners, dyes and auxiliaries, are probed and determined through emission product spectra in incident and/or transmitted light by a photon detector using an emission spectroscopie process, characterised in that the different luminescent substances in the layers and layer assemblages are photosensitively determined alongside one another in a single measurement by synchronously changing the emission wavelength $\lambda_e$ and the excitation wavelength $\lambda_a$, offset by the substance related free choice of the wavelength difference $\Delta\lambda$, through the wavelengths $\lambda$ and measuring the emission.

2. A process as claimed in claim 1, characterised in that unpolarised light is used for exciting the sample for emission and an angle of 55° or 125° is selected between the directions of the emission and excitation beams so that emission is unaffected by the viewing direction.

3. A process as claimed in claim 1, characterised in that linearly polarised light is used for exciting the sample for emission.

4. In the process as claimed in claim 1 rotating on a fixed axis a first grating whereby the excitation wavelength $\lambda_a$ is obtained, and rotating on a fixed axis a second grating whereby the emission wavelength $\lambda_e$ is obtained as characterised by offsetting the respective rotations to provide the wavelength difference.

5. A process as claimed in claim 1 for the layer-selective detection of coating flaws in the individual layers and layer assemblages, including the step of probing the layers by lasers, by very narrow bands and the shape and size of the measuring spot beamed or radiated onto the layer is adaptable to the flaws to be detected.

6. A process as claimed in claim 1, characterised in that luminescent substances, such as optical lighteners, spectral sensitisers and dyes, are added to the solutions for forming the layers before they are applied in such low concentrations that the properties of the layers are not adversely affected.

7. A process as claimed in claim 1, characterised in that influences in other layers are eliminated by using the exciting light reflected by the sample as reference and correcting the emission therewith.

* * * * *